(12) United States Patent
Benninghoff et al.

(10) Patent No.: US 8,461,174 B2
(45) Date of Patent: Jun. 11, 2013

(54) TREATMENT FOR CUTANEOUS METASTASES

(75) Inventors: Bernd Benninghoff, Affalterthal (DE); Ulrich R Hengge, Essen (DE)

(73) Assignee: 3M Innovative Properties Company, St. Paul, MN (US)

( * ) Notice: Subject to any disclaimer, the term of this patent is extended or adjusted under 35 U.S.C. 154(b) by 974 days.

(21) Appl. No.: 11/722,891

(22) PCT Filed: Dec. 30, 2005

(86) PCT No.: PCT/US2005/047467
§ 371 (c)(1),
(2), (4) Date: Aug. 28, 2009

(87) PCT Pub. No.: WO2006/071997
PCT Pub. Date: Jul. 6, 2006

(65) Prior Publication Data
US 2010/0056557 A1   Mar. 4, 2010

Related U.S. Application Data

(60) Provisional application No. 60/640,491, filed on Dec. 30, 2004.

(51) Int. Cl.
*A61K 31/44* (2006.01)

(52) U.S. Cl.
USPC .................................................. 514/293

(58) Field of Classification Search
None
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gerster |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,693,811 A | 12/1997 | Lindstrom |
| 5,741,908 A | 4/1998 | Gerster et al. |
| 5,756,747 A | 5/1998 | Gerster et al. |
| 5,939,090 A | 8/1999 | Beaurline et al. |
| 6,028,076 A | 2/2000 | Hirota et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,388 B1 | 2/2001 | Krieg et al. |
| 6,194,425 B1 | 2/2001 | Gerster et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,303,347 B1 | 10/2001 | Johnson et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,376,501 B1 | 4/2002 | Isobe et al. |
| 6,376,669 B1 | 4/2002 | Rice et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,451,810 B1 | 9/2002 | Coleman et al. |
| 6,476,000 B1 | 11/2002 | Agrawal |
| 6,518,265 B1 | 2/2003 | Kato et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |

(Continued)

FOREIGN PATENT DOCUMENTS

| | | |
|---|---|---|
| EP | 0 394 026 | 10/1990 |
| EP | 1 104 764 | 6/2001 |

(Continued)

OTHER PUBLICATIONS

Nashan et al. J. Cancer Res. Clin. Oncol., 2009, vol. 135, pp. 1-14.*

(Continued)

*Primary Examiner* — James D Anderson

(57) ABSTRACT

The present invention provides methods for treating cutaneous metastases. In one aspect, the method can include identifying a treatment area that comprises one or more lesions containing metastatic cells; and administering an IRM compound to the treatment area in an amount effective for treating the lesion. In another aspect, the method can include identifying a treatment area that comprises one or more lesions containing metastatic cells; and administering a TLR7 agonist to the treatment area in an amount effective for treating the lesion. In another aspect, the method can include identifying a treatment area that comprises one or more lesions containing metastatic cells; and administering a TLR8 agonist to the treatment area in an amount effective for treating the lesion.

9 Claims, 4 Drawing Sheets

U.S. PATENT DOCUMENTS

| | | | |
|---|---|---|---|
| 6,573,273 B1 | 6/2003 | Crooks et al. |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,465 B2 | 2/2004 | Dellaria et al. |
| 6,706,728 B2 | 3/2004 | Hedenstrom et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,818,650 B2 | 11/2004 | Griesgraber |
| 6,841,678 B2 | 1/2005 | Merli et al. |
| 6,852,861 B2 | 2/2005 | Merli et al. |
| 6,894,060 B2 | 5/2005 | Slade |
| 7,125,836 B2 | 10/2006 | Woodward |
| 7,163,947 B2 | 1/2007 | Griesgraber et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2003/0072760 A1 | 4/2003 | Sirbasku |
| 2003/0096835 A1 | 5/2003 | Crooks et al. |
| 2003/0130299 A1 | 7/2003 | Crooks et al. |
| 2003/0133913 A1 | 7/2003 | Tomai et al. |
| 2003/0139364 A1 | 7/2003 | Krieg et al. |
| 2003/0144286 A1 | 7/2003 | Frenkel et al. |
| 2003/0161797 A1 | 8/2003 | Miller et al. |
| 2003/0199461 A1 | 10/2003 | Averett et al. |
| 2003/0199538 A1 | 10/2003 | Skwierczynski et al. |
| 2004/0014779 A1 | 1/2004 | Gorden et al. |
| 2004/0076633 A1 | 4/2004 | Thomsen et al. |
| 2004/0091491 A1 | 5/2004 | Kedl et al. |
| 2004/0132079 A1 | 7/2004 | Gupta et al. |
| 2004/0141950 A1 | 7/2004 | Noelle et al. |
| 2004/0147543 A1 | 7/2004 | Hays et al. |
| 2004/0162309 A1 | 8/2004 | Gorden et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Lee et al. |
| 2004/0181130 A1 | 9/2004 | Fox et al. |
| 2004/0181211 A1 | 9/2004 | Elliott et al. |
| 2004/0191833 A1 | 9/2004 | Fink et al. |
| 2004/0192585 A1 | 9/2004 | Owens et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2005/0054590 A1 | 3/2005 | Averett |
| 2005/0085500 A1 | 4/2005 | Gutman et al. |
| 2005/0119273 A1 | 6/2005 | Lipford et al. |
| 2005/0136065 A1 | 6/2005 | Valiante |
| 2005/0165236 A1 | 7/2005 | Colombo et al. |
| 2005/0245562 A1 | 11/2005 | Garcia-Echeverria et al. |

FOREIGN PATENT DOCUMENTS

| | | |
|---|---|---|
| JP | 9-208584 | 8/1997 |
| JP | 11-080156 A | 3/1999 |
| JP | 11-222432 | 8/1999 |
| JP | 2000-247884 | 9/2000 |
| WO | WO 00/75304 | 12/2000 |
| WO | WO 02/08905 | 1/2002 |
| WO | WO 02/36592 | 5/2002 |
| WO | WO 03/045391 | 6/2003 |
| WO | WO 2005/018551 | 3/2005 |
| WO | WO 2005/018555 | 3/2005 |
| WO | WO 2005/018556 | 3/2005 |
| WO | WO 2005/020999 | 3/2005 |
| WO | WO 2005/032484 | 4/2005 |
| WO | WO 2005/048933 | 6/2005 |
| WO | WO 2005/048945 | 6/2005 |
| WO | WO 2005/051317 | 6/2005 |
| WO | WO 2005/051324 | 6/2005 |
| WO | WO 2005/054237 | 6/2005 |
| WO | WO 2005/054238 | 6/2005 |
| WO | WO 2005/066169 | 7/2005 |
| WO | WO 2005/066170 | 7/2005 |
| WO | WO 2005/066172 | 7/2005 |
| WO | WO 2005/076783 | 8/2005 |
| WO | WO 2005/079195 | 9/2005 |
| WO | WO 2005/089317 | 9/2005 |
| WO | WO 2005/094531 | 10/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO 2006/065280 | 6/2006 |
| WO | WO 2006/074003 | 7/2006 |
| WO | WO 2006/074046 | 7/2006 |
| WO | WO 2006/004737 | 8/2006 |
| WO | WO 2006/083400 | 8/2006 |
| WO | WO 2006/083440 | 8/2006 |
| WO | WO 2006/086449 | 8/2006 |
| WO | WO 2006/086633 | 8/2006 |
| WO | WO 2006/091394 | 8/2006 |
| WO | WO 2006/091567 | 8/2006 |
| WO | WO 2006/091568 | 8/2006 |
| WO | WO 2006/091647 | 8/2006 |
| WO | WO 2006/098852 | 9/2006 |
| WO | WO 2006/107771 | 10/2006 |
| WO | WO 2006/107851 | 10/2006 |
| WO | WO 2006/107853 | 10/2006 |
| WO | WO 2006/121528 | 11/2006 |
| WO | WO 2007/028129 | 3/2007 |
| WO | WO 2007/030775 | 3/2007 |
| WO | WO 2007/030777 | 3/2007 |
| WO | WO 2007/035935 | 3/2007 |
| WO | WO 2007/056112 | 5/2007 |

OTHER PUBLICATIONS

Schon et al. J. Natl. Cancer Inst., 2003, vol. 95, pp. 1138-1149.*

Bong et al. Dermatology, 2002, vol. 205, No. 2, pp. 135-138 (ABSTRACT attached).*

Spaner et al. Leuk. Lymphoma, 2005, vol. 46, No. 6, pp. 935-939.*

Dockrell et al. Journal of Antimicrobial Chemotherapy, 2001, vol. 48, pp. 751-755.*

Ugurel S. et al., "Topical imiquimod eradicates skin metastases of malignant melanoma but fails to prevent rapid lymphogenous Metastatic spread." Sep. 2002, The British Journal of Dermatology, vol. 147, Nr. 3, pp. 621-624, XP002521150 ISSN: 007-0963.

Wolf Ingrid H. et al., "Locoregional cutaneous metastases of malignant melanoma and their management," Dermatology Surgery: Official publication for American Society for Dermatologic Surgery, Feb. 2004, vol. 30, No. 2 pt. 2, pp. 244-247, XP002521146, ISSN: 1076-0512.

Hesling C., et al., "In vivo and in situ modulation of the expression of genes involved in metastasis and angiogenesis in a patient treated with topical imiquimod for melanoma skin metastases," The British Journal of Dermatology. Apr. 2004, vol. 150, No. 4, pp. 761-767, XP002521147, ISSN: 007-0963.

Schon Michael P. et al., "Death receptor-independent adoptosis in malignant melanoma induced by the small-molecule immune response modifier imiquimod," The Journal of Investigative Dermatology, May 2004, vol. 122, No. 5, pp. 1266-1276, XP002521148, ISSN: 0022-202X.

Database Medline [Online] U.S. National Library of Medicine (NLM), Bethsda, MD, US; Sep. 2002, Moore Susan: "Cutaneous metastatic breast cancer," XP002521151, Database accession No. NLM112240484, & Clinical Journal of Oncology Nursing, vol. 6, No. 5, pp. 255-260, ISSN: 1092-1095.

Schwartz Robert A. et al: "Secondary mucinous carcinoma of the skin: metastatic breast cancer," Dermatologic Surgery: Official publication for American Society for Dermatologic Surgery [et al.]. Feb. 2004, vol. 30, No. 2, pt. 1, pp. 234-235, XP002521149, ISSN. 1076-0512.

Database Medline [Online] U.S. National Library of Medicine (NLM), Bethesda, MD, U.S.; Feb. 2003, Krathen Richard A. et al: "Cutaneous metastasis: a meta-analysis of data," XP002521152, Database accession No. NLM12630642 & Southern Medical Journal, vol. 96, No. 2, pp. 164-167, ISSN 0038-4348.

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

Brennan et al., "Automated Bioassay of Interferons in Micro-test Plates.", *Biotechniques*, June/July, 78, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-astriazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).

Henge et al., "Topical Imiquimod to Treat Recurrent Breast Cancer" *Breast Cancer Research and Treatment* (2005).

Wolf et al., "Topical Imiquinod in the Treatment of Metastatic Melanoma to Skin", *Arch Dermatol* vol. 139, Mar. 2003 pp. 273-276.

Suchin et al., "Treatment of Stage IA Cutaneous T-Cell Lymphoma With Topical Application of the Immune Response Modifier Imiquimod", *Arch Dermatol* vol. 138, Sep. 2002, pp. 1137-1139.

Steinmann et al., "Topical Imiquinod Treatment of a Cutaneous Melanoma Metastasis—Letter to the editor"., *J AM Acad Dermatol*, Sep. 2000, pp. 555-556.

Heil et al., *Science*, vol. 303, pp. 1526-1529, Mar. 5, 2004.

\* cited by examiner

TREATMENT FOR CUTANEOUS METASTASES

CROSS REFERENCE TO RELATED APPLICATIONS

This application is a national stage filing under 35 U.S.C. 371 of PCT/US2005/047467, filed Dec. 30, 2005, which claims priority to U.S. application Ser. No. 60/640,491, filed Dec. 30, 2004, the disclosure of which is incorporated by reference in its/their entirety herein.

BACKGROUND

Cutaneous metastases are secondary tumors associated with many different types of cancer. They occur when cancerous cells break away from a primary tumor and become established as secondary tumors. Metastatic tumors often cause accelerated deterioration of the patient's condition and, therefore, can be fatal. Cutaneous metastases occur as a result of one or more metastatic processes that can include, for example, primary tumor proliferation, local extension, vascular and/or lymphatic penetration and embolization, accidental transfer of malignant cells during diagnostic or surgical procedures, and release of malignant cells.

Cutaneous metastases occur in up to about 9% of all cancer patients, but occur most frequently in connection with breast cancer in women and in connection with lung cancer in men. Melanoma, ovarian, oral cavity, renal, colon, and gastric primary cancers account for about 90% of all cutaneous metastases.

Patients typically present with rapidly developing nodules or tumors, often on chest, scalp, neck, abdomen, or back. Less frequent sites include the upper extremities and the pelvis. Patients may report pain, tenderness, and/or infection. Cutaneous metastases are characterized by tumor invasion with capillary rupture, necrosis, and infection, which can result in a purulent, friable, and malodorous lesion. Cutaneous metastases may show characteristics of the primary tumor. In other cases, however, cells of the metastatic tumor may become at least partially undifferentiated.

Treatment of cutaneous metastases depends, at least in part, on the treatment of the primary tumor. Often, this can include systemic therapy, but can also include local treatments including, for example, surgical excision, irradiation, chemotherapy, cryotherapy, laser therapy, or hormone therapy. The side effects of many such treatments are well characterized.

Social isolation, embarrassment, even ostracism can result from disfigurement and/or odor associated with cutaneous metastases. Therefore, effective treatment of cutaneous metastases can significantly enhance a patient's quality of life and may even prolong a patient's life. There is an existing need to find additional effective treatments for cutaneous metastases that result in fewer or less severe side affects and may prolong life.

SUMMARY

It has been found that certain small molecule IRMs can be used to treat cutaneous metastases. Accordingly, the present invention provides a method of treating a cutaneous metastasis in a patient in need of such treatment. Generally, the method includes identifying a treatment area that comprises one or more lesions containing metastatic cells; and administering an IRM compound to the treatment area in an amount effective for treating the lesion.

In another aspect, the present invention also provides a method of treating a cutaneous metastasis in a patient in need of such treatment. Generally, the method includes identifying a treatment area that comprises one or more lesions containing metastatic cells; and administering a TLR7 agonist to the treatment area in an amount effective for treating the lesion.

In another aspect, the present invention also provides a method of treating a cutaneous metastasis in a patient in need of such treatment. Generally, the method includes identifying a treatment area that comprises one or more lesions containing metastatic cells; and administering a TLR8 agonist to the treatment area in an amount effective for treating the lesion.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

Figure 1A:
FIG. 1A shows an irregular inflammatory erythema on the left shoulder of a patient.
Figure 1B:
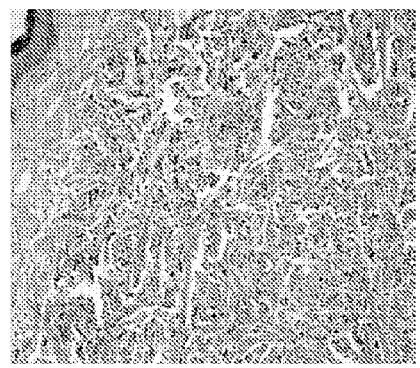
FIG. 1B shows histological examination of a biopsy taken from the irregular inflammatory erythema shown in FIG. 1A.
Figure 1C:
FIG. 1C shows immunohistological examination of a biopsy taken from the irregular inflammatory erythema shown in FIG. 1A.
Figure 1D:
FIG. 1D shows immunohistological examination of a biopsy taken from the irregular inflammatory erythema shown in FIG. 1A.
Figure 1E:
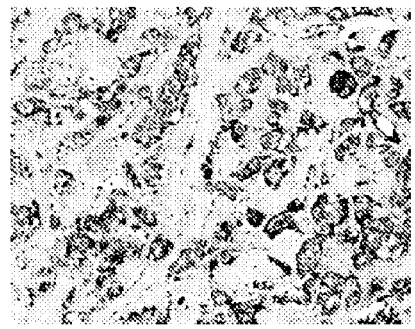
FIG. 1E shows immunohistological examination of a biopsy taken from the irregular inflammatory erythema shown in FIG. 1A.

It has now been found that certain immune response modifier (IRM) compounds may provide effective treatment of cutaneous metastases. Generally, IRM compounds can act by stimulating certain key aspects of the immune system, as well as by suppressing certain other aspects. Certain IRM compounds appear to act through Toll-like receptors (TLRs) to induce selected cytokine biosynthesis, induction of co-stimulatory molecules, and increased antigen-presenting capacity. Certain compounds (e.g., IRM compounds and/or TLR agonists) can provide effective treatment of cutaneous metastases when topically administered to the area of the skin affected by the cutaneous metastasis. Often, patients affected by cutaneous metastases are undergoing radiation and/or chemotherapy for the primary tumor and may not easily tolerate additional radiation and/or chemotherapy to manage the cutaneous metastasis. Therefore, the present invention provides an alternative treatment for cutaneous metastases that is simple, non-invasive, well tolerated, and effective.

The cutaneous metastasis may arise from any type of primary cancer such as, for example, breast, lung, melanoma, head and neck, ovarian, oral cavity, renal, colon, or gastric primary cancer. In some embodiments, the primary cancer may be a solid tumor such as, for example, breast cancer or lung cancer. In certain embodiments, the primary cancer is a Her2/neu-positive breast cancer. In other embodiments, the primary cancer is a Her2/neu-negative breast cancer.

The cutaneous metastasis may be an intradermal metastasis, i.e., a secondary tumor located between the layers of the skin. Moreover, the metastatic process may involve the lymphatic system, and so may be characterized as a lymphatic metastasis.

Certain IRMs are small organic molecules (e.g., molecular weight under about 1000 Daltons, preferably under about 500 Daltons, as opposed to large biological molecules such as proteins, peptides, and the like) such as those disclosed in, for example, U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; and 6,818,650; U.S. Patent Publication Nos. 2004/0091491; 2004/0147543; and 2004/0176367; and International Publication Nos. WO 2005/18551, WO 2005/18556, WO 2005/20999, WO 2005/032484, WO 2005/048933, WO 2005/048945, WO 2005/051317, WO 2005/051324, WO 2005/066169, WO 2005/066170, WO 2005/066172, WO 2005/076783, and WO 2005/079195.

Additional examples of small molecule IRMs include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/08905), certain 3-β-D-ribofuranosylthiazolo[4,5-d]pyrimidine derivatives (such as those described in U.S. Publication No. 2003/0199461), and certain small molecule immuno-potentiator compounds such as those described, for example, in US2005/0136065.

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG sequences and are described, for example, in International Patent Publication No. WO 00/75304. Still other IRM nucleotide sequences include guanosine- and uridine-rich single-stranded RNA (ssRNA) such as those described, for example, in Heil et al., *Science*, vol. 303, pp. 1526-1529, Mar. 5, 2004.

Other IRMs include biological molecules such as aminoalkyl glucosaminide phosphates (AGPs) and are described, for example, in U.S. Pat. Nos. 6,113,918; 6,303,347; 6,525,028; and 6,649,172.

Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

In some embodiments of the present invention, the IRM compound may be an agonist of at least one Toll-like receptor (TLR) such as, for example, TLR7 or TLR8. The IRM may also in some cases be an agonist of TLR9. In certain embodiments, the IRM compound may be a TLR7 agonist and/or a TLR8 agonist. In certain specific embodiments, the IRM compound may be a TLR7/8 agonist.

As used herein, "agonist" refers to a compound that can combine with a receptor (e.g., a TLR) to induce a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the receptor. Thus, an agonist may be referred to as an agonist of a particular TLR (e.g., a TLR7-selective agonist) or a particular combination of TLRs (e.g., a TLR 7/8 agonist—an agonist of both TLR7 and TLR8).

As used herein, the term "TLR7-selective agonist" refers to any compound that acts as an agonist of TLR7, but does not act as an agonist of TLR8. A "TLR8-selective agonist" refers to a compound that acts as an agonist of TLR8, but does not act as an agonist of TLR7.

A TLR7-selective agonist or a TLR8-selective agonist may act as an agonist for the indicated TLR and one or more of TLR1, TLR2, TLR3, TLR4, TLR5, TLR6, TLR9, or TLR10. Accordingly, while "TLR7-selective agonist" may refer to a compound that acts as an agonist for TLR7 and for no other TLR, it may alternatively refer to a compound that acts as an agonist of TLR7 and, for example, TLR6. Similarly, "TLR8-selective agonist" may refer to a compound that acts as an agonist for TLR8 and for no other TLR, but it may alternatively refer to a compound that acts as an agonist of TLR8 and, for example, TLR6.

The TLR agonism for a particular compound may be assessed in any suitable manner. For example, assays and recombinant cell lines suitable for detecting TLR agonism of test compounds are described, for example, in U.S. Patent Publication Nos. US2004/0014779, US2004/0132079, US2004/0162309, US2004/0171086, US2004/0191833, and US2004/0197865.

Regardless of the particular assay employed, a compound can be identified as an agonist of a particular TLR if performing the assay with a compound results in at least a threshold increase of some biological activity mediated by the particular TLR. Conversely, a compound may be identified as not acting as an agonist of a specified TLR if, when used to perform an assay designed to detect biological activity mediated by the specified TLR, the compound fails to elicit a threshold increase in the biological activity. Unless otherwise indicated, an increase in biological activity refers to an increase in the same biological activity over that observed in an appropriate control. An assay may or may not be performed in conjunction with the appropriate control. With experience, one skilled in the art may develop sufficient familiarity with a particular assay (e.g., the range of values observed in an appropriate control under specific assay conditions) that performing a control may not always be necessary to determine the TLR agonism of a compound in a particular assay.

The precise threshold increase of TLR-mediated biological activity for determining whether a particular compound is or is not an agonist of a particular TLR in a given assay may vary according to factors known in the art including but not limited to the biological activity observed as the endpoint of the assay, the method used to measure or detect the endpoint of the assay, the signal-to-noise ratio of the assay, the precision of the assay, and whether the same assay is being used to determine the agonism of a compound for two or more TLRs. Accordingly it is not practical to set forth generally the threshold increase of TLR-mediated biological activity required to identify a compound as being an agonist or a non-agonist of a particular TLR for all possible assays. Those of ordinary skill in the art, however, can readily determine the appropriate threshold with due consideration of such factors.

Assays employing HEK293 cells transfected with an expressible TLR structural gene may use a threshold of, for example, at least a three-fold increase in a TLR-mediated biological activity (e.g., NFκB activation) when the compound is provided at a concentration of, for example, from about 1 µM to about 10 µM for identifying a compound as an agonist of the TLR transfected into the cell. However, different thresholds and/or different concentration ranges may be suitable in certain circumstances. Also, different thresholds may be appropriate for different assays.

In some embodiments of the present invention, the IRM compound may be a small molecule immune response modifier (e.g., molecular weight of less than about 1000 Daltons).

In some embodiments of the present invention, the IRM compound may include a 2-aminopyridine fused to a five membered nitrogen-containing heterocyclic ring, or a 4-aminopyrimidine fused to a five membered nitrogen-containing heterocyclic ring.

IRM compounds suitable for use in the invention include compounds having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, hydroxylamine substituted imidazoquinoline amines, oxime substituted imidazoquinoline amines, 6-, 7-, 8-, or 9-aryl, heteroaryl, aryloxy or arylalkyleneoxy substituted imidazoquinoline amines, and imidazoquinoline diamines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, hydroxylamine substituted tetrahydroimidazoquinoline amines, oxime substituted tetrahydroimidazoquinoline amines, and tetrahydroimidazoquinoline diamines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; pyrazolopyridine amines; pyrazoloquinoline amines; tetrahydropyrazoloquinoline amines; pyrazolonaphthyridine amines; tetrahydropyrazolonaphthyridine amines; and 1H-imidazo dimers fused to pyridine amines, quinoline amines, tetrahydroquinoline amines, naphthyridine amines, or tetrahydronaphthyridine amines.

In certain embodiments, the IRM compound may be an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, a thiazolonaphthyridine amine, a pyrazolopyridine amine, a pyrazoloquinoline amine, a tetrahydropyrazoloquinoline amine, a pyrazolonaphthyridine amine, or a tetrahydropyrazolonaphthyridine amine.

In one embodiment, the IRM compound may be an imidazoquinoline amine such as, for example, 1-(2-methylpropyl)-1H-imidazo[4,5-c]quinolin-4-amine or 4-amino-α,α-dimethyl-2-ethoxymethyl-1H-imidazo[4,5-c]quinolin-1-ethanol.

Suitable IRM compounds also may include the purine derivatives, imidazoquinoline amide derivatives, benzimidazole derivatives, adenine derivatives, aminoalkyl glucosaminide phosphates, and oligonucleotide sequences described above.

The IRM compound may be provided in any formulation suitable for administration to a subject. Suitable types of formulations are described, for example, in U.S. Pat. No. 5,238,944; U.S. Pat. No. 5,939,090; U.S. Pat. No. 6,245,776; European Patent No. EP 0 394 026; International Patent Publication No. WO 03/045391; International Patent Publication No. WO 05/089317; and U.S. Patent Publication No. 2003/0199538.

The compound may be provided in any suitable form including but not limited to a solution, a suspension, an emulsion, or any form of mixture. The compound may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including but not limited to adjuvants, skin penetration enhancers, colorants, fragrances, moisturizers, thickeners, and the like. In certain embodiments, the formulation may be delivered topically.

The composition of a formulation suitable for practicing the invention will vary according to factors known in the art including but not limited to the physical and chemical nature of the IRM compound, the nature of the carrier, the intended dosing regimen, the state of the subject's immune system (e.g., suppressed, compromised, stimulated), the nature of the primary tumor, the nature of the metastatic tumor, the method of administering the IRM compound, and the species to which the formulation is being administered. Accordingly, it is not practical to set forth generally the composition of a formulation effective for treating cutaneous metastases for all possible applications. Those of ordinary skill in the art, however, can readily determine an appropriate formulation with due consideration of such factors.

In some embodiments, the methods of the present invention include administering IRM to a subject in a formulation of, for example, from about 0.0001% to about 20% (unless otherwise indicated, all percentages provided herein are weight/weight with respect to the total formulation) to the subject, although in some embodiments the IRM compound may be administered using a formulation that provides IRM compound in a concentration outside of this range. In certain embodiments, the method includes administering to a subject a formulation that includes from about 0.01% to about 5% IRM compound, for example, a formulation that includes about 1% to about 5% IRM compound.

In one embodiment, the formulation may be a cream such as that described, for example, in U.S. Pat. No. 5,238,944 that includes about 5% 1-(2-methylpropyl)-1H-imidazo[4,5-c]quinolin-4-amine.

In another embodiment, the formulation may be a gel such as that described, for example, in U.S. Pat. No. 5,939,090 that contains from about 0.01% to about 1.0% 4-amino-α,α-dimethyl-2-ethoxymethyl-1H-imidazo[4,5-c]quinolin-1-ethanol. One particular embodiment includes a gel formulation such as that described, for example, in U.S. Pat. No. 5,939,090, that contains about 0.02% 4-amino-α,α-dimethyl-2-ethoxymethyl-1H-imidazo[4,5-c]quinolin-1-ethanol. Another particular embodiment includes a gel formulation such as that described, for example, in U.S. Pat. No. 5,939,090, that contains about 0.06% 4-amino-α,α-dimethyl-2-ethoxymethyl-1H-imidazo[4,5-c]quinolin-1-ethanol.

In another embodiment, the formulation may be a cream such as that described, for example, in International Patent Publication No. WO 05/089317, that contains from about 0.03% to about 0.3% 2-methyl-1-(2-methylpropyl)-1H-imidazo[4,5-c]naphthyridin-4-amine.

In another embodiment, the formulation may be a cream such as that described, for example, in International Patent Publication No. WO 05/089317, that contains from about 0.01% to about 1.0% N-[4-(4-amino-2-ethyl-1H-imidazo[4,5-c]quinolin-1-yl)butyl]methanesulfonamide.

In yet another embodiment, the formulation may be a cream such as that described, for example, in International Patent Publication No. WO 05/089317, that contains from about 0.01% to about 1.0% N-[2-(4-amino-2-ethoxymethyl-1H-imidazo[4,5-c]quinolin-1-yl)-1,1-dimethylethyl]methanesulfonamide.

An amount of an IRM compound effective for treating a cutaneous metastasis is an amount sufficient to slow the growth or spreading of the metastatic tumor. In some cases, an amount of an IRM compound effective for treating a cutaneous metastasis is an amount effective to reduce the size of the metastatic tumor even, in some cases, to the point of completely clearing the metastatic tumor. The precise amount of IRM compound necessary for treating a cutaneous metastasis will vary according to factors known in the art including but not limited to the physical and chemical nature of the IRM compound, the nature of the carrier, the intended dosing regimen, the state of the subject's immune system (e.g., suppressed, compromised, stimulated), the nature of the primary tumor, the nature of the metastatic tumor, the method of administering the IRM compound, and the species to which the formulation is being administered. Accordingly, it is not practical to set forth generally the amount that constitutes an amount of IRM compound effective for treating cutaneous metastases for all possible applications. Those of ordinary skill in the art, however, can readily determine the appropriate amount with due consideration of such factors.

In some embodiments, the methods of the present invention include administering sufficient IRM compound to provide a dose of, for example, from about 100 ng/kg to about 50 mg/kg to the subject, although in some embodiments the methods may be performed by administering IRM compound in a dose outside this range. In some of these embodiments, the method includes administering sufficient IRM compound to provide a dose of from about 10 µg/kg to about 5 mg/kg to the subject, for example, a dose of about 100 µg/kg to about 1 mg/kg.

The dosing regimen may depend at least in part on many factors known in the art including but not limited to the physical and chemical nature of the IRM compound, the nature of the carrier, the amount of IRM being administered, the state of the subject's immune system (e.g., suppressed, compromised, stimulated), the nature of the primary tumor, the nature of the metastatic tumor, the method of administering the IRM compound, and the species to which the formulation is being administered. Accordingly it is not practical to set forth generally the dosing regimen effective for treating a cutaneous metastasis for all possible applications. Those of ordinary skill in the art, however, can readily determine an appropriate dosing regimen with due consideration of such factors.

In some embodiments of the invention, the dosing regimen can include administering the IRM compound, for example, from a single dose to about multiple doses per week. In certain embodiments, the IRM compound may be administered from about once per week to about once per day. In one particular embodiment, the IRM compound is administered five times per week.

In some embodiments, the dosing regimen may include administering the IRM compound, for example, from a single dose to a period of many months. In some cases, the IRM compound may be administered for a period necessary to resolve or clear the metastatic tumor. Thus, treatment may be terminated upon clearance of the metastatic tumor as determined by any suitable method such as, for example, gross examination, biopsy, or other histological method. In alternative embodiments, the IRM compound may be administered for a predetermined period of from about two weeks to about two years. In some of these embodiments, the IRM compound may be administered from about two months to about twelve months, for example, for about six months.

The methods of the present invention may be performed on any suitable subject. Suitable subjects include but are not limited to animals such as but not limited to humans, non-human primates, rodents, dogs, cats, horses, pigs, sheep, goats, or cows.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

The IRM compound used in the examples is 1-(2-methylpropyl)-1H-imidazo[4,5-c]quinolin-4-amine, formulated as a 5% cream available under the tradename ALDARA (3M Co., St. Paul, Minn.).

Example 1

A 65-year old woman with breast cancer (UICC stage pT1c, pN1b1, M0, G2, estrogen-positive, progesterone-positive) developed an axillary recurrence and osteolytic metastases (L2-4) despite axillary dissection and neoadjuvant and adjuvant chemotherapy. The recurrent tumor and metastases were treated with radiation. Nine months later, the breast cancer recurred locally (rpT1c, M1, G2, estrogen-negative, progesterone-negative, Her2/neu-positive) and was treated with trastuzumab and percutaneous radiation. An inflammatory erythema occurred on the upper back (FIG. 1A). On histology, invasive lobular tumor cells (keratin-positive, Her2/neu-positive, ICAM-1-positive) were present (FIGS. 1B-1E.

Figure 1F:
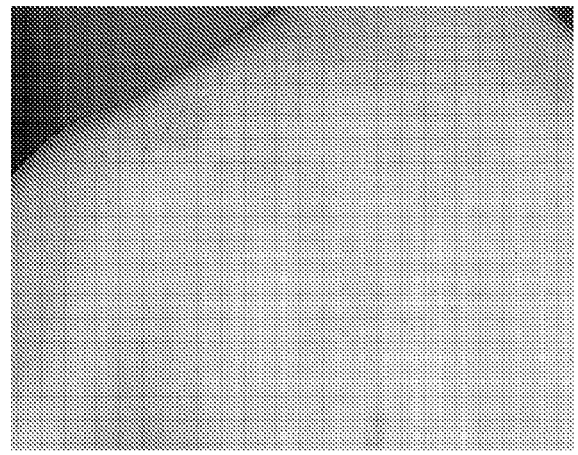
FIG. 1F shows the area of the irregular inflammatory erythema shown in FIG. 1A after treatment with an IRM compound.
Figure 1G:
FIG. 1G shows histological examination of the area after treatment with an IRM compound.
Figure 1H:
FIG. 1H shows immunohistological examination of the area after treatment with an IRM compound.

1-(2-methylpropyl)-1H-imidazo[4,5-c]quinolin-4-amine was administered topically five times per week for six months. After the treatment period, no skin lesions were detected upon gross examination or histological examination (FIGS. 1F-1H). The patient has remained free of cutaneous metastasis for more than ten months.

Example 2

Figure 1I:
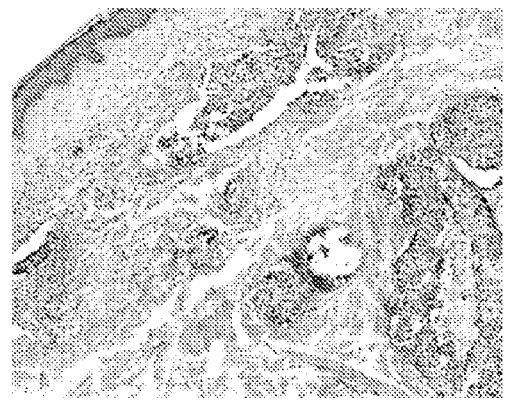
FIG. 1I shows histological examination of cutaneous metastasis of invasive ductal carcinoma before treatment with an IRM compound.

A 41-year old woman with invasive ductal carcinoma (UICC stage T2, pN1, B2, cM0) that was estrogen-negative, progesterone-negative, and Her2/neu-negative was treated by mastectomy and adjuvant chemotherapy. Infraclavicular and supraclavicular recurrences were treated with γ- and telecobalt radiation, intrarterial and intravenous chemotherapy. A diffuse cutaneous lesion occurred on the scapula that, upon histological examination, contained an infiltrative ductal growth pattern (FIG. 1I).

Figure 1J:
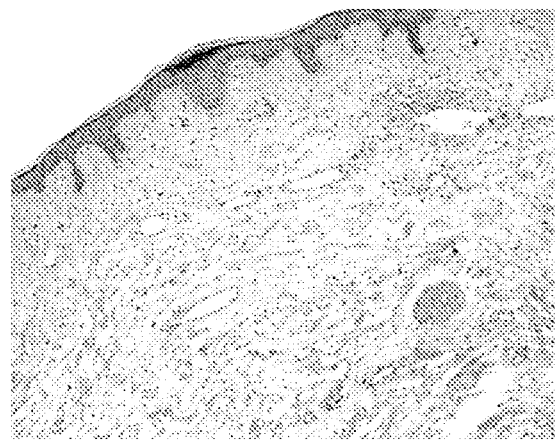
FIG. 1J shows histological examination of cutaneous metastasis of invasive ductal carcinoma after treatment with an IRM compound.

1-(2-methylpropyl)-1H-imidazo[4,5-c]quinolin-4-amine was administered topically five times per week for six months. After the treatment period, a skin biopsy of an affected area was free of carcinoma cells (FIG. 1J).

The complete disclosures of the patents, patent documents and publications cited herein are incorporated by reference in their entirety as if each were individually incorporated. In case of conflict, the present specification, including definitions, shall control.

Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method of treating a cutaneous metastasis derived from a breast cancer tumor in a patient in need of such treatment, comprising:
   (a) identifying a treatment area that comprises one or more lesions containing metastatic cells; and
   (b) administering an immune response modifier (IRM) compound selected from the group consisting of: 1-(2-methylpropyl)-1H-imidazo[4,5-c]quinolin-4-amine and 4-amino-α,α-dimethyl-2-ethoxymethyl-1H-imidazo[4,5-c]quinolin-1-ethanol to the treatment area in an amount effective for treating the lesion.

2. The method of claim 1 wherein the IRM compound is administered topically.

3. The method of claim 1 wherein the IRM compound is 4-amino-α,α-dimethyl-2-ethoxymethyl-1H-imidazo[4,5-c]quinolin-1-ethanol.

4. The method of claim 1 wherein the IRM compound is administered at least once per week.

5. The method of claim 1 wherein the IRM compound is administered at least five times per week.

6. The method of claim 1 wherein the IRM compound is administered for at least four weeks.

7. The method of claim 1 wherein the IRM compound is administered for at least six months.

8. The method of claim 1 wherein the breast cancer tumor is Her2/neu-positive.

9. The method of claim 1 wherein the breast cancer tumor is Her2/neu-negative.

* * * * *